US006987274B1

(12) United States Patent  
Street et al.

(10) Patent No.: US 6,987,274 B1  
(45) Date of Patent: Jan. 17, 2006

(54) LIGHT DETECTION AND IMAGING SYSTEM AND METHOD INCLUDING AN ARRAY OF SENSORS

(75) Inventors: Robert A. Street, Palo Alto, CA (US); Patrick Y. Maeda, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 10/929,579

(22) Filed: Aug. 31, 2004

(51) Int. Cl.  
*G01N 21/64* (2006.01)

(52) U.S. Cl. .................................. 250/458.1
(58) Field of Classification Search ........... 250/458.1  
See application file for complete search history.

(56) References Cited

U.S. PATENT DOCUMENTS 6,169,289 B1 * 1/2001 White et al. ............. 250/458.1
6,317,206 B1 * 11/2001 Wulf ........................ 356/317
2002/0197634 A1 * 12/2002 Emoto ........................ 435/6

\* cited by examiner

*Primary Examiner*—David Porta  
*Assistant Examiner*—Marcus Taningco  
(74) *Attorney, Agent, or Firm*—Oliff & Berridge, PLC

(57) ABSTRACT

A light detection system for imaging an object including a light source, an object, a first substrate with a sensor arranged on a side of the first substrate opposite from the light source, the sensor having an opening through which the light from the light source passes. A distance from the sensor to the object corresponds approximately to the size of the sensor. The light illuminates the object and the sensor detects the light emanating from the object. The object is scanned relative to the sensor to create the image. A method includes arranging the sensor to face the object, illuminating the object with a light source so that the light passes through the opening in the sensor, and detecting the light emanating from the object, the object being scanned relative to the sensor to create the image.

21 Claims, 8 Drawing Sheets

LIGHT DETECTION AND IMAGING SYSTEM AND METHOD INCLUDING AN ARRAY OF SENSORS

BACKGROUND OF THE INVENTION

1. Field of Invention

The invention relates to systems and methods for detecting light using a sensor. More specifically, the systems and methods of the invention relate to an imaging detector that includes an array of sensors.

2. Description of Related Art

Fluorescence illumination and observation is a rapidly expanding microscopy technique employed today. This microscopy technique may be used in both the medical and biological sciences. Because the microscopy technique is rapidly expanding, sophisticated microscopes and numerous fluorescence accessories have been developed. For example, Epi-fluorescence, or incident light fluorescence, is used in many applications. The technique of fluorescence microscopy has become an essential tool in biology and the biomedical sciences, as well as in materials science due to attributes that are not readily available in other contrast modes with traditional optical microscopy. The application of an array of fluorochromes has made it possible to identify cells and sub-microscopic cellular components with a high degree of specificity among non-fluorescing material. In fact, the fluorescence microscope is capable of revealing the presence of a single molecule. Through the use of multiple fluorescence labeling, different probes can simultaneously identify several target molecules.

Fluorescence microscopy includes a process in which susceptible molecules emit light from electronically excited states created by either a physical (for example, absorption of light), mechanical (friction), or chemical mechanism. The generation of luminescence through excitation of a molecule by ultraviolet or visible light photons is a phenomenon termed photoluminescence, which may be divided into two categories: fluorescence and phosphorescence. Each process depends upon the electronic configuration of the excited state and the emission pathway. The absorption and subsequent re-radiation of light by organic and inorganic specimens is generally the result of the fluorescence or phosphorescence. The fluorescence process uses the ability of some atoms and molecules to absorb light at a particular wavelength and to subsequently emit light of longer wavelength after a brief interval. The process of phosphorescence occurs in a manner similar to fluorescence, but with a much longer excited state duration. The emission of light through the fluorescence process is nearly simultaneous with the absorption of the excitation light. When emission persists longer after the excitation light has been extinguished, the phenomenon is referred to as phosphorescence.

The modern fluorescence microscope may combine the power of high performance optical components with computerized control of the instrument and digital image acquisition to achieve a level of sophistication that far exceeds that of simple observation by the human eye. The fluorescence microscopy generally depends on electronic imaging to rapidly acquire information at low light levels or at visually undetectable wavelengths.

In contrast to other modes of optical microscopy that are based on macroscopic specimen features (such as phase gradients, light absorption, and birefringence), fluorescence microscopy may image the distribution of a single molecular species based solely on the properties of fluorescence emission. Thus, using fluorescence microscopy, a precise location of intracellular components labeled with specific fluorophores may be monitored, as well as their associated diffusion coefficients, transport characteristics, and interactions with other biomolecules. In addition, the response in fluorescence to localized environmental variables enables the investigation of pH, viscosity, refractive index, ionic concentrations, membrane potential, and solvent polarity in living cells and tissues.

One benefit of fluorescence microscopy is its ability to detect fluorescent objects that are sometimes faintly visible or even very bright relative to the dark (often black) background. In order to achieve this benefit, image brightness and resolution must be maximized by ensuring that the object or sample is supplied with sufficient light energy for excitation at the appropriate wavelength for each chromophore attached to the specimen. Moreover, a selection of a proper filter will maximize the amount of emitted fluorescence directed to the sensor.

Two examples of commonly used light detectors used in fluorescence microscopy are the photomultiplier tube (PMT) and the photodiode. Both devices employ a photosensitive surface that captures incident photons and generates electronic charges that are sensed and amplified. PMTs are commonly used in confocal microscopes and high-end automatic exposure bodies for film cameras as well as in spectrometers. These devices respond when photons impinge on a photocathode and liberate electrons that are accelerated toward an electron multiplier composed of a series of curved plates (known as dynodes). Conventional methods that use a single detector such as a single PMT to detect light, or illuminate the object broadly and detect the light using a pixel array may not properly detect the emitted fluorescence light. For example, the detection using these methods may be unsatisfactory and relatively slow because a single detector is used in the device with the PMT. Moreover, a weak signal may result when broadly scanning the pixel array thus making detection of the light even more difficult.

Silicon photodiodes may also be used to respond rapidly to light by the generation of a current. Uniformity of the photosensitive surface is excellent and the dynamic range and response speed of these devices are among the highest of any light detector. However, conventional arrangements using the silicon photodiodes have a relatively flat response over the entire visible spectrum. Moreover, conventional arrangements of silicon diodes as sensors may also produce a considerable amount of noise, (much of it thermal) resulting in relatively poor signal-to-noise under photon-limited conditions.

Fluorescence microscopes may be used to irradiate the specimen with a desired and specific band of wavelengths, and then to separate the much weaker emitted fluorescence from the excitation light. Ideally, only the emission light should reach the detector so that the resulting fluorescent structures are superimposed with high contrast against a very dark (or black) background. However, conventional devices do not properly detect the emitted fluorescence light in this manner using conventional sensor arrangements.

Some conventional systems perform detection by putting a lens in front of the fixed point and a detector behind the lens. The detector collects all of the light that was emitted through the lens. However, in these systems, not all of the light is collected and detected, which poses a particular problem if the angular distribution of the emission is large. Moreover, the time required to accurately detect using this system is excessive.

When the detection device uses the PMT imager scanned across the plate, or a charge-coupled device (CCD) to image a line, the time necessary for imaging is excessive. In the case of a CCD, the detector is optically coupled to the capillary array by way of the capillaries in the array being optically coupled to the linearly aligned pixels. However, this method is disadvantageous because the illumination at any given cell is generally very-weak, and the optical coupling between the object and detector may be unsatisfactory when a large field of view is needed.

If the conventional fluorescence detection device includes PMTs, CCDs, optical filters, lenses and lasers, the detection system may tend to be bulky resulting in problems that can arise because of the size of the detections systems. Fluorescent detection processes are very sensitive, especially when they are combined with laser excitation. However, the detection systems of the prior techniques pose many problems in the efficiency of sequencing and imaging. For example, some fixed end detection systems require up to eight hours in order to detect one sample. Further, by using a prior art detector, all of the possible data may not be collected. Another reason that the prior art detection systems are not efficient is that these systems typically only detect one band at a time, e.g. the band that has reached the end of the separation apparatus in fixed end detection.

SUMMARY OF THE INVENTION

Based on the problems-discussed above, the invention combines scanned illumination with an array of detectors to form a compact device with good optical sensitivity and high speed processing without a need for focusing optics. The invention may be a form of microscope that detects emitted light, for example, fluorescent light, without having to use focusing devices.

In various exemplary embodiments of the invention, a light detection system for imaging an object includes a light source, an object, and a first substrate with a sensor arranged on a side of the first substrate opposite from the light source. The sensor has an opening through which the light from the light source passes. A distance from the sensor to the object corresponds approximately to the size of the sensor. The light illuminates the object and the sensor detects the light emanating from the object. The object is scanned relative to the sensor to create the image.

In various alternative embodiments of the invention, a method includes arranging the sensor to face the object, illuminating the object with a light source so that the light passes through the opening in the sensor, and detecting the light emanating from the object, the object being scanned relative to the sensor to create the image.

In various exemplary embodiments, the systems and methods further provide increased performance at a lower cost as compared to the conventional methods discussed above because a single illumination source may efficiently illuminate an object and a plurality of sensors, for example, an array of sensors without using an objective lens.

In various alternative embodiments of the invention, optical filters may be used to effectively absorb the primary illumination allowing the fluorescence light at a different wavelength to pass through the filter and be detected by the sensor. The filters may be integrated onto a sensor chip in order to reduce the resulting size of the system and overall costs. Moreover, baffles may be used to improve the detection of the light from the object.

In various alternative embodiments of the invention, existing spinners or other physical scanners may be used in the detections systems.

Using various exemplary embodiments, a focused laser may be scanned over a large number of sensors in an array to detect reflected light emitted by a few tagged cells. Furthermore, specific cells present in various small concentrations may be located, e.g., the rare cell problem.

BRIEF DESCRIPTION OF THE DRAWINGS

Various exemplary embodiments of the systems and methods according to the invention will be described in detail, with reference to the following figures, wherein.

DETAILED DESCRIPTION OF EXEMPLARY EMBODIMENTS

Figure 1:
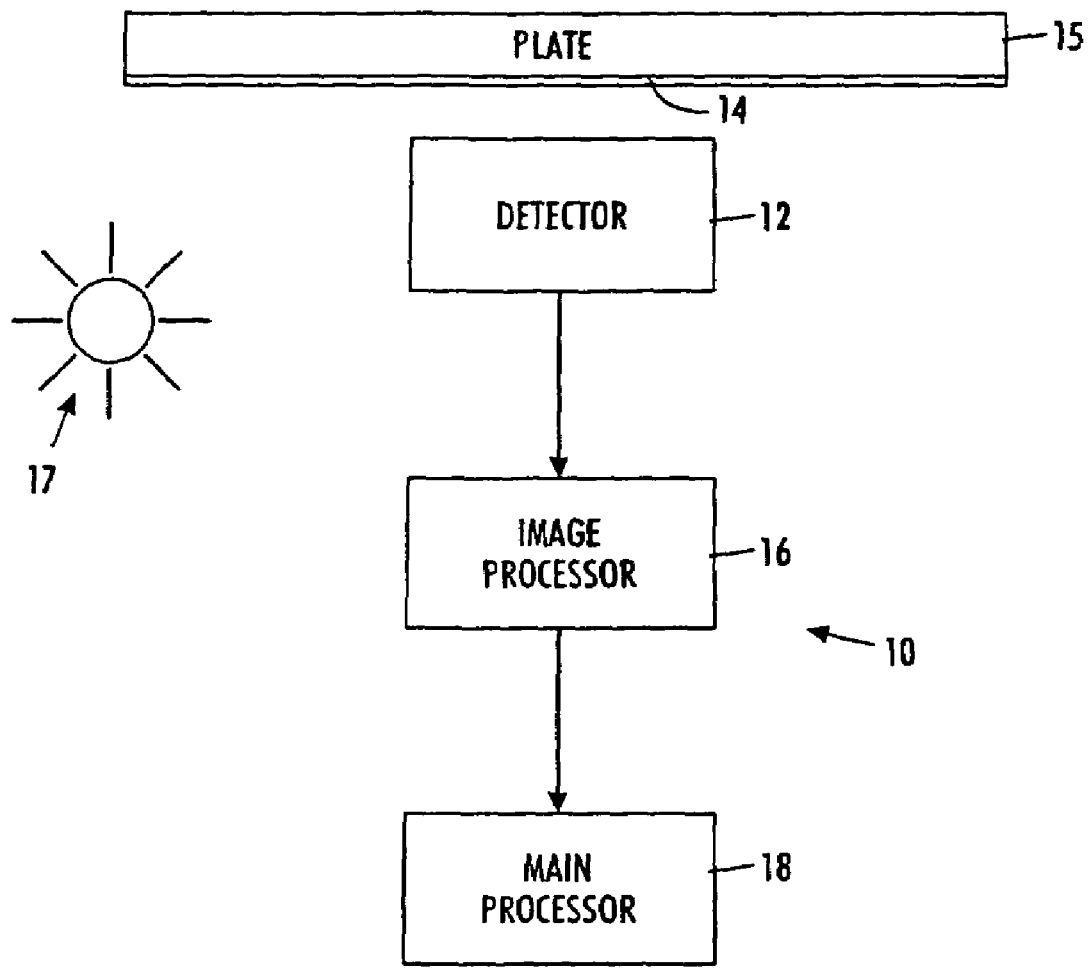
FIG. 1 is an exemplary diagram of a detection system in accordance with an embodiment of the invention.

The invention relates generally to systems and methods of imaging an object using a scanned array of detectors operated by imaging. With reference now to the drawings wherein the showings (which generally only representatively show the elements) are for purposes of illustrating the features of the invention and not for purposes of limiting the same, FIG. 1 shows a system 10 for imaging an object or a sample. A detector 12 detects the emission of light from a sample or object 14 disposed on a substrate that may include a plate 15. After an illumination source 17 illuminates the object 14, the detector 12 scans the entire plate 15 at predetermined points in time to obtain the necessary data. The data collected by the detector 12 (which represents an image of a region of interest on the object 14 at a given time) is then processed by an image processor 16. Based on the resultant processed data provided by the image processor 16, an image is created.

The detector may sense fluorescence or reflected light from the object 14. In the case of fluorescence, the object 14 is either naturally fluorescent or is made to be fluorescent, for example, imaging a cluster of cells which are tagged with fluorescent markers. In general, the detector 12 may include an optical filter that prevents the illumination light from passing, but allows the fluorescence, which is at a different wavelength, to pass. The detector 12 may also be used to image the reflected light from the object. In this case, an optical filter may be used to select the color of light to be imaged, if broadband illumination (for example white light) is used. For convenience, the examples provided below may use fluorescent light as the light imaged from the object.

However, it should be appreciated that the invention may be configured to detect reflected light or any other form of light emission from the object without departing from the sprit and scope of the invention.

Also shown in FIG. 1 is the illumination source 17 which may include a laser, e.g. an argon laser or semiconductor diode laser, illuminating across the plate 15 in a direction perpendicular to the plate. The illumination may also occur in a direction parallel to the migration. The illumination source 17 may be disposed on an edge of a detector bar and a detector array could be disposed on an opposite edge, or rear, of the detector bar.

It should be appreciated by one skilled in the art that the image processing and other data processing is accomplished based on imaging and processing technology that is well known in the art. For example, the techniques of scanning an object to obtain rasterized data that can then be processed as image data are well known and may be readily implemented. In this regard, various hardware and software techniques could be implemented without departing from the spirit and the scope of the invention.

Figure 2:
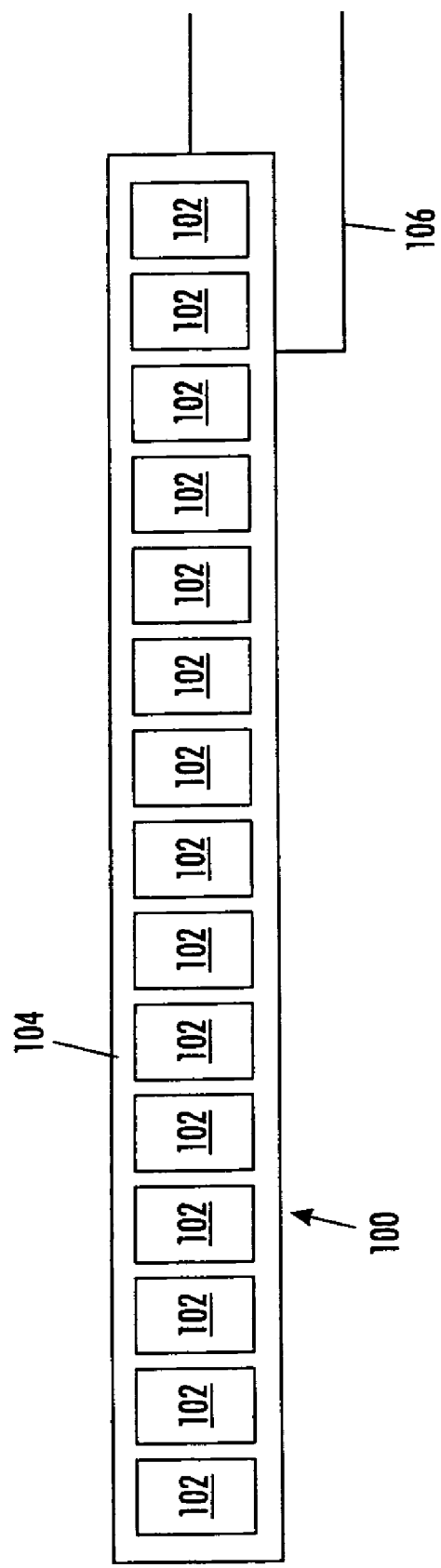
FIG. 2 is an exemplary diagram of a detector array in accordance with an embodiment of the invention.

It should also be appreciated by one skilled in the art that either a single sensor, or a one-dimensional array or a two-dimensional array of sensors can be used as the detector 12. A detector array 100 is shown in FIG. 2 and may include a plurality of sensors 102 that are assembled on a base member or bar 104. The sensors 102 may be aligned in an end to end relation to form a composite scanning array or chip. The detector array 100 may include a rectangular base or bar 104 (which may be glass), with a plurality of sensors 102 arranged in a linear row or array on one surface. The sensor rows may be parallel to the side edge of the array base. Operation of the sensors may be controlled by cooperating control circuitry, such as logic gates and a shift register, which is measured through the use of a data readout line 106. The row of sensors may be extended to the end of the array base to permit an array to be abutted to other like arrays. The detector array 100 may be scanned over an area associated with each sensor 102, e.g., 3×3 mm, and the detected signal is read out simultaneously from all the sensors 102 which greatly increases performance. Imaging may be performed by mechanical raster scanning of the detector array 100 along with the illumination source 17 relative to the object 14, for example, either the detector 12 or the object 14 plane can be scanned. Scanning is only required over the small area that is detected by a single sensor 102. The other sensors 102 scan equivalent areas simultaneously to give the full image.

The use of different detectors may allow the implementation of a varying range of wavelengths. For example, the detector may use crystalline silicon and be sensitive from about 400 to about 900 nanometers, while the amorphous silicon arrays (described in more detail below) may be sensitive from about 400 to about 700 nanometers. Both of these types of detectors span a range that is wide enough to detect the fluorescence emission.

Figure 3:
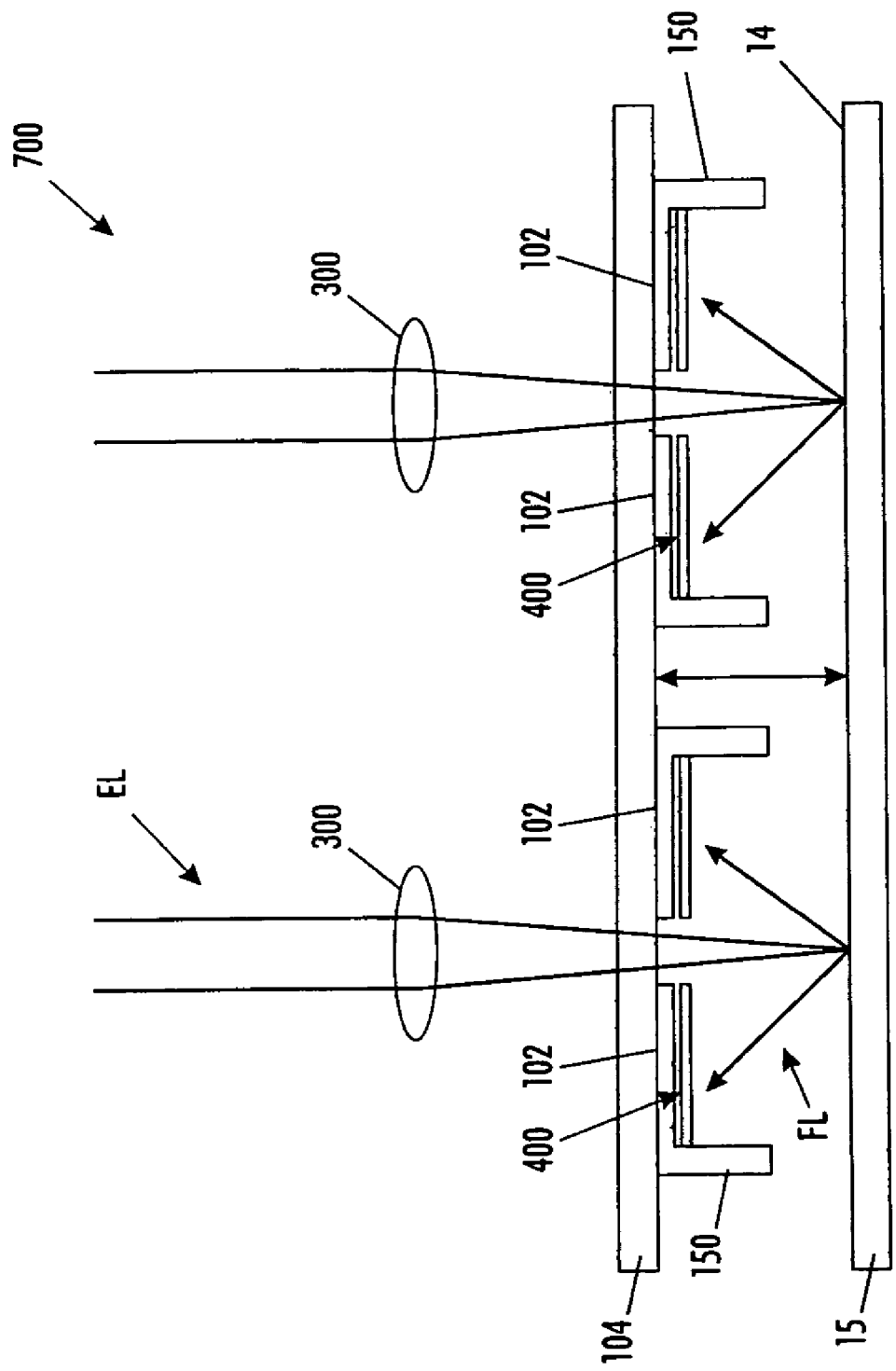
FIG. 3 is an exemplary diagram of an array of sensors in accordance with an embodiment of the invention.

As shown in FIG. 3, two elements of an array of sensors for detecting, for example, fluorescence imaging from an object 14 are shown in the detector structure 700 that is part of the detector 12. The detector structure 700 may include the rectangular base or bar 104 that includes sensors 102, filters 400 and baffles 150. The illumination source 17 (not shown) provides the excitation light EL which focuses on an object 14 that may include excitation material. The sensors 102 may be photodiodes that detect reflected light such as the fluorescence FL that reflects off of the object 14 as the fluorescence radiates into the hemisphere. The filters 400 may include material with an absorption edge that has a range of a specific wavelength. For example, the filters may include different dielectric material and can be interference filters. The baffles 150 are optional and may prevent fluorescence from leaking over into another sensor area and contributing to false detections.

The optional baffles 150 at the side of the sensor 102 may serve to:

(a) prevent emission from one sensor 102 from being detected by an adjacent sensor; and
(b) reflect the fluorescent light FL directly into the sensor 102 to improve the sensitivity of the sensor 102. These objects may be achieved by forming the baffle 150 of a light absorbing or reflective material. The baffles 150 may also be formed by patterning and coating SU8 or by a conventionally manufactured structure.

As shown in FIG. 3, the illumination source (not shown) provides the excitation light EL which may pass through an optical lens 300 to focus the excitation light on the object 14. The optical lens 300 may have operational characteristics that are well known and focuses the excitation light onto a fixed point on the object 14. As discussed above, conventional systems may position the lens 300 in front of a fixed point and position a detector behind the lens. Using this configuration, the detector may fail to collect all of the light that was emitted through the lens. However, in various exemplary embodiments, and as shown in FIG. 3, the optical lens 300 may be positioned on an opposite side of the rectangular base or bar 104 from the sensors 102. Thus, an increased amount of fluorescent light FL is collected and detected because the sensors 102 and the filter 400 have an non-obstructed view of the object 14.

Figure 4:
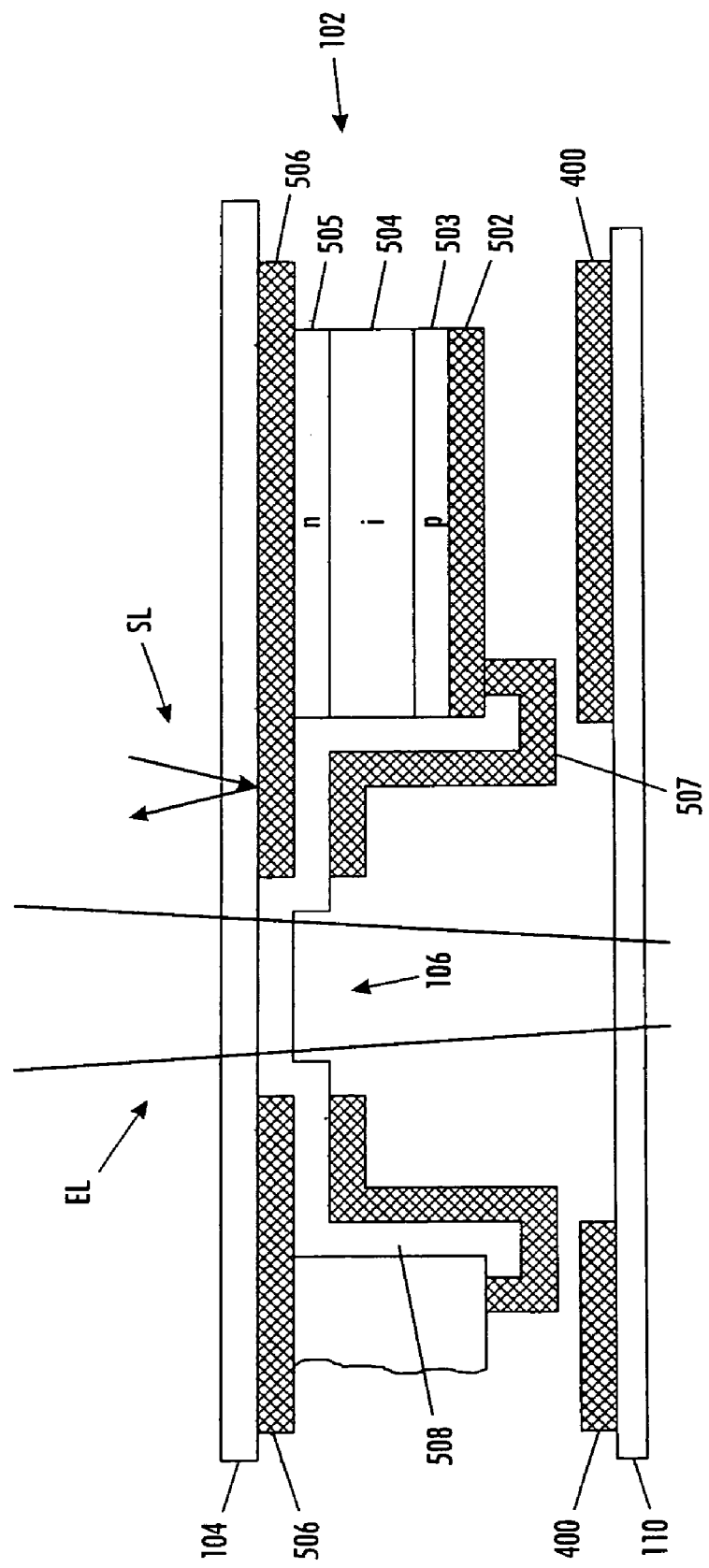
FIG. 4 is an exemplary diagram of a detailed structure of a sensor in accordance with an embodiment of the invention.
Figure 5:
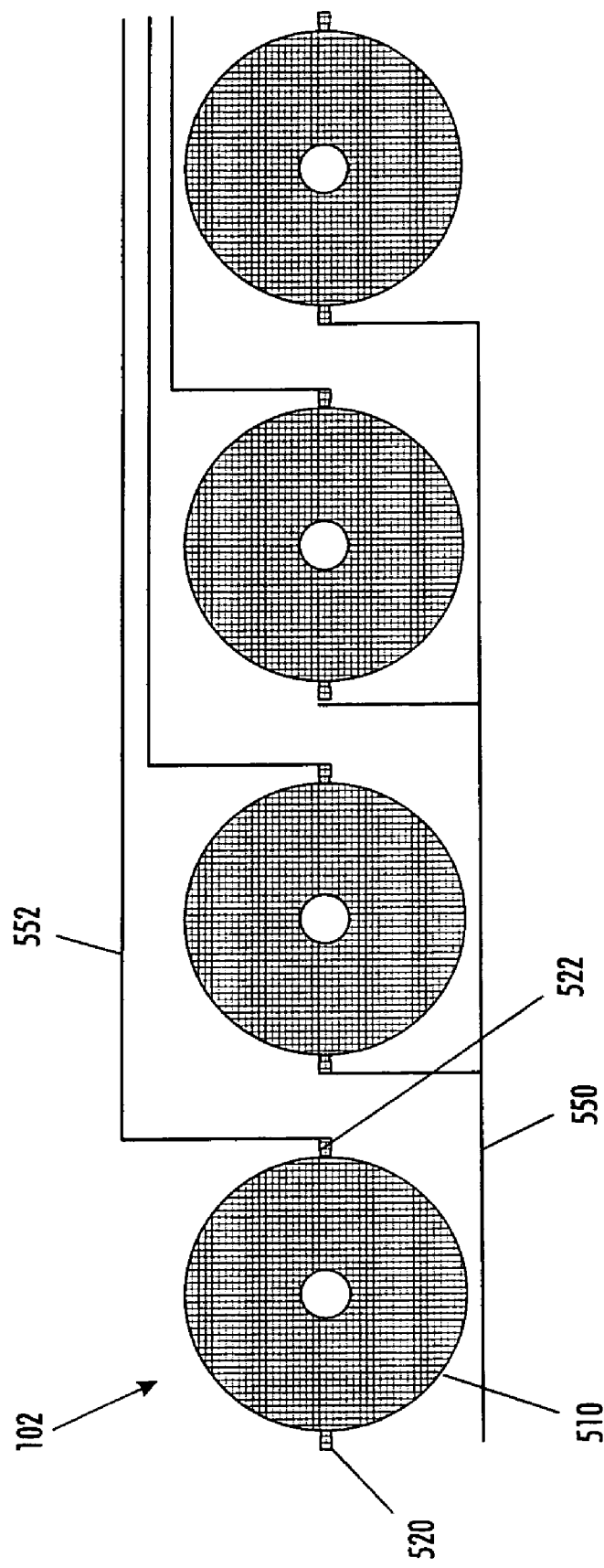
FIG. 5 is an exemplary diagram of a plan view of the array of sensors in accordance with an embodiment of the invention.

FIG. 4 shows a more detailed diagram of one of the sensors 102 in the detector array 100 shown in FIG. 2 and the detector structure 700 shown in FIG. 3. As shown in FIG. 4, the sensor 102 may be an amorphous silicon photodiode placed close to the object 14 plane. An amorphous silicon photodiode is a solid-state device that converts light into electric current. A cross section of photodiode used as the sensor 102 in FIG. 4 includes an n-type silicon layer 505, a p-type silicon layer 503, and an intrinsic (or undoped) layer 504, forming a p-i-n junction between the p-type silicon layer 503 and the n-type silicon layer 505. The sensor 102 may be formed with thickness of approximately 1 micron, and configured to have a high rejection of the direct excitation illumination. The sensor 102 may formed on a substrate like the rectangular base or bar 104 and the sensor 102 may include a hole 510 to allow the excitation light to pass through. The hole in the sensor 102 is shown in FIG. 5. The sensor 102 may be positioned so that the distance d (FIG. 3) from the sensor 102 to the base member or bar 104 corresponds approximately to the size of the sensor 102. For example, if the sensor 102 is a 2×2 mm device, then the sensor 102 may be positioned 0.5–1.0 mm from the base member or bar 104.

The photodiode senses visible light and converts the light into electric current. The photodiode also may have a high quantum efficiency in the wavelength range of 400 to 650 nm. Any suitable amorphous or polycrystalline sensor material may be used, for example, alloys of amorphous silicon, organic sensor materials and polycrystalline semiconductors such as $HgI_2$ and $PbI_2$. Alternatively, it would be possible to configure the detector array 100 with individual single crystal detectors such as silicon avalanche photodiodes or even using a microchannel plate configured to the appropriate geometry. These options may be used to provide an increased sensitivity of the detector. Single crystal silicon can be used with a hole etched in the silicon substrate, or alternatively a thin layer of single crystal silicon attached to a substrate such as glass, as is known in the art It should be appreciated by one skilled in the art that any known photodiode device may be used as the sensor 102 without departing from the spirit and scope of the invention.

The hole in the sensor 102 may allow the illumination source 17, for example, a focused laser or LED beam, to illuminate the object 14. The spatial resolution of the imaging may be determined by the spot size, perhaps 1–30 microns. The size of the hole depends on the focusing of the illumination source, and may be in the range 50–500 micron. The light collection efficiency depends on the size of the sensor and the distance to the object, and for a 2 mm sensor placed 1 mm from the object, the efficiency may be about 15%. A thin film optical filter 400 may be formed on a substrate 110 and placed near the sensor 102 to absorb the reflected excitation illumination, but allow the fluorescent light FL to pass. The optical filter 400 may also be positioned directly on top of the sensor to protect the sensor 102 from unwanted scattered excitation illumination.

A first electrode 506 may be formed between the sensor 102 and the rectangular base or bar 104. The first electrode 506 may be formed with an opaque metal material to prevent the excitation light EL from being detected by the sensor 102. A second electrode 502 may be formed on an opposite side of the sensor 102 from the first electrode 506. The second electrode 502 may be transparent and formed of indium tin oxide (ITO) to allow the fluorescent light to be detected by the sensor 102. At the edge of the sensor 102, near the illumination hole 106, there may be formed an insulation layer 508 and a metal layer 507 of opaque material (or other material) over the insulation layer 508 that covers the edge of the sensor 102 to prevent any scattered light SL from being detected. Another optional metal layer (not shown) acting as a light shield may be formed on a side opposite the sensor 102 from the metal layer 507.

A plan view of the sensors 102 is shown in FIG. 5 which illustrates the configuration of the hole 510 in the sensor 102 and the electrical connections. As shown in FIG. 5, each sensor 102 includes the hole 510 and a pair of electrical terminals 520 and 522. The electrical terminals 520 and 522 may be common electrodes known in the art. The electrical terminals 520 and 522 are connected to links 550 and 552 which are connected to a power source. As previously discussed, operation of the sensors 102 may be controlled by cooperating control circuitry, such as logic gates and a shift register, which is measured through the use of the data readout line 106. Once the sensors 102 have detected signals, the detected signals may be read out simultaneously from all of the sensors 102 to improve efficiency and performance. The best position for the illumination hole 510 is in the center of the sensor 102 to provide the highest sensitivity detection of the scattered light SL, but if necessary the illumination hole 501 could be at the side of the sensor 102 or on any other part of the sensor 102.

For a small number of sensors 102, e.g., up to about 100, individual connections can be made to the readout electronics. If a larger number of sensors 102 are used, then a standard matrix addressing scheme may be used such as a scheme used for conventional sensor arrays. In either situation, the image signal is preferably sent to a charge sensitive amplifier (not shown) for processing which may be included in the image processor 16 or main processor 18. Correlated double sampling can be used to remove background illumination and some noise sources.

Figure 6:
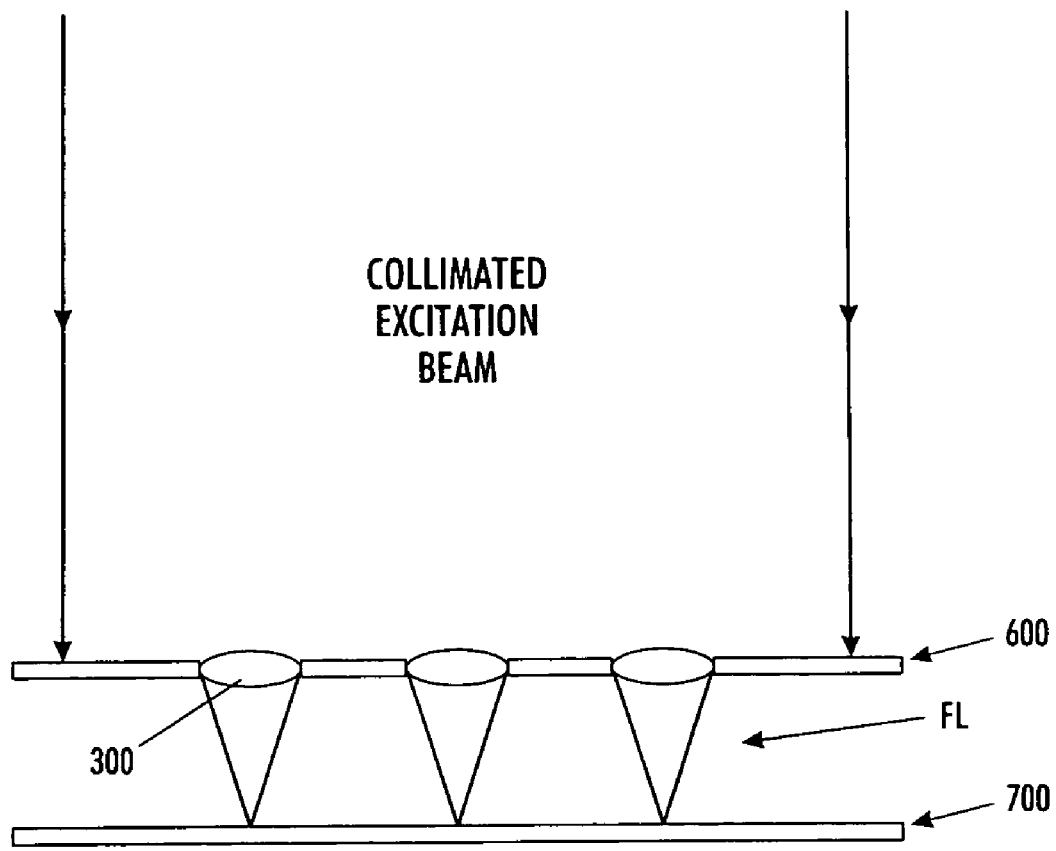
FIG. 6 is an exemplary diagram showing a an embodiment of illumination in accordance with the invention.
Figure 7:
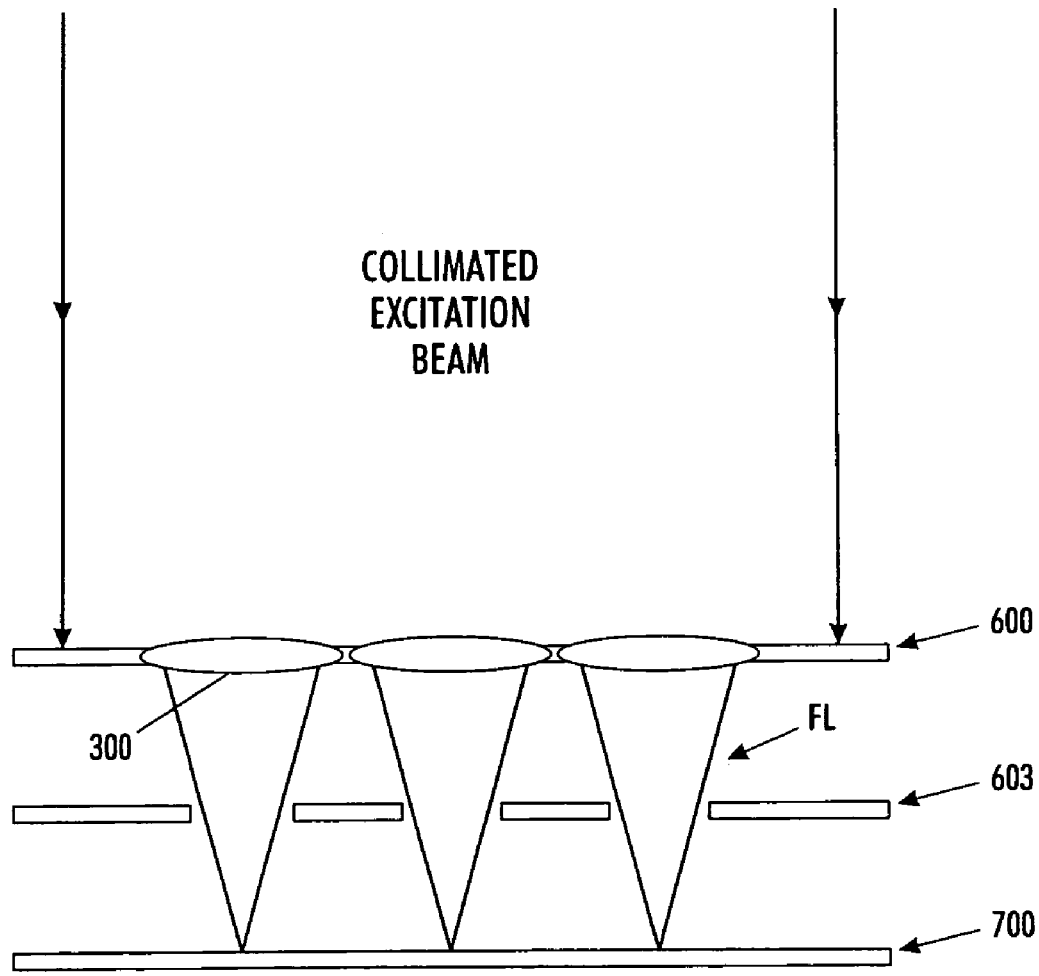
FIG. 7 is an exemplary diagram showing another embodiment of illumination in accordance with the invention.
Figure 8:
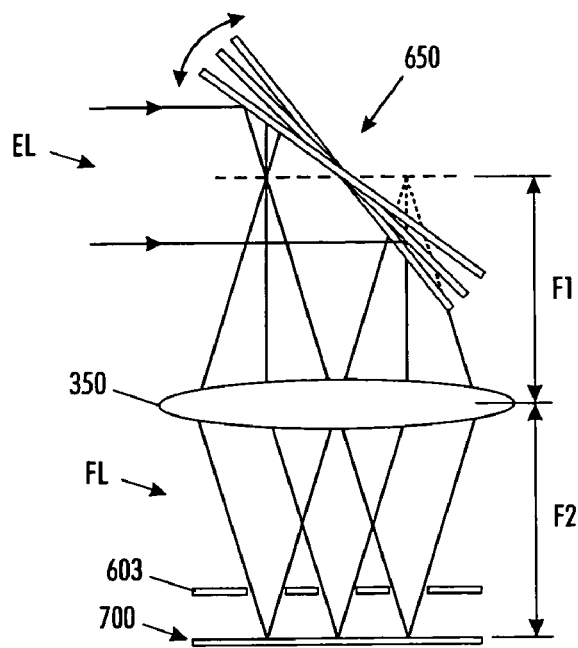
FIG. 8 is an exemplary diagram showing another embodiment of illumination in accordance with the invention.
Figure 9:
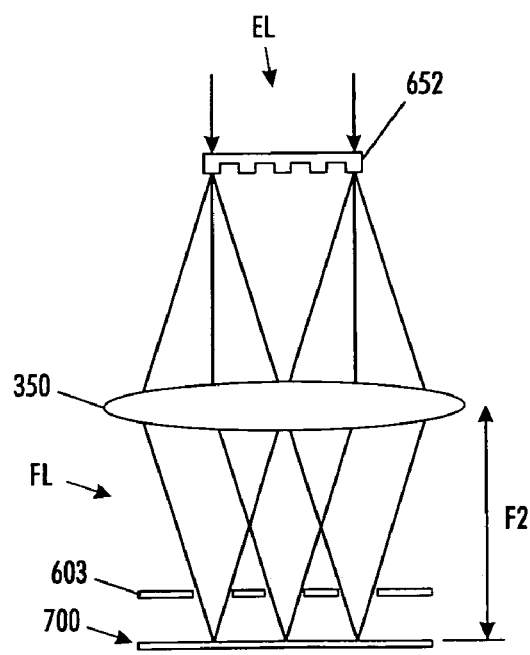
FIG. 9 is an exemplary diagram of another embodiment of illumination in accordance with the invention.

In various exemplary embodiments, the illumination source 17 providing the illumination may have an individual diode laser or LED for each sensor 102, which will work if there is not a large number of sensors 102. Optional lenses 300 or an optional micro-lens array 600 or 602 may be used to focus the illumination as shown in FIGS. 1 and 6–9. For a larger number of sensors 102, a beam deflector or diffractive optical element may be used as shown in FIGS. 8–9 to scan or distribute a laser beam from sensor to sensor. Flood illumination with a large collimated laser beam may also be employed. As shown in FIGS. 6 and 7, a collimated excitation beam from the illumination source 17 is directed through the micro-lens array 600 and 603 to focus an increased amount of the illumination source 17 both on the object 14 and the detection array 100 with a higher efficiency. The base member or bar 603 with openings may assist in positioning the light from the lens 300 to the object 14.

FIG. 8 is an exemplary diagram showing another embodiment of illumination in accordance with the invention. As shown in FIG. 8, only one lens 350 is used instead of the micro-lens array in FIGS. 6 and 7. The illumination in FIG. 8 may be performed in sequence and the light beam from the excitation light EL is scanned across the lens 350 using the scanning mirror 650 as a beam deflector. The lens 350 may be a telecentric objective lens, where the center of scanning mirror is set to a distance F1 from the objective lens, where F1 is equal to the front focal length of the objective lens, and the detector structure 700 is set to a distance F2 from the objective lens, where F2 is equal to the back focal length of the objective lens. By varying the position of the scanning mirror 650 and its distance F1 from the lens 350, the entire excitation light beam may be deflected onto the lens 350 as reflected light, and may also be adjusted to focus on a particular sensor 102 within the detector structure 700. Thus, the system in FIG. 8 functions to multiplex the entire excitation light beam onto different sensors 102 within the detector structure 700. If the fluorescent light is weak, this configuration may be used to focus more light on one sensor 102 to view an improved image of the object 14.

FIG. 9 is an exemplary diagram of another embodiment of illumination in accordance with the invention. As shown in FIG. 9, a grating or hologram 652 is included in the system as a diffractive optical element which receives the excitation light beam and generates a plurality of collimated beams directed at angles that correspond to the angular position of each sensor 102 in the detection structure 700. The system in FIG. 9 may also use a single lens 350 instead of the micro-lens array in FIGS. 6 and 7, and because the grating or hologram 652 is used instead of the scanning mirror 650 in FIG. 8, the resulting system is smaller and thus increases space savings. Furthermore, the system in FIG. 9 also functions to divide and direct the excitation light beam onto different sensors 102 within the detector structure 700.

The detection sensitivity using the various exemplary embodiments of the invention depends on many factors, but one example is provides below for fluorescence detection. If it assumed that an incident illumination beam for each sensor 102 has a power of 10 microwatts, or about $10^{13}$ photons/seconds, that the absorption by the object 14 is 10% and the fluorescence efficiency is 10%, then the emitted fluorescence is approximately $10^{11}$ photons/seconds, the optical collection efficiency should be approximately 15%, and the sensor quantum efficiency is approximately 80%, giving approximately $10^{10}$ electrons/seconds of detected charge. The capacitance of the sensor 102 assuming a 2×2 mm device is approximately 400 pF, and the corresponding kTC electronic noise of the sensor 102 is about 10,000 electrons. If a measurement is made every 1 msec, then the signal is $10^7$ electrons and the signal-to-noise ratio is 1,000, which is sufficient to reach satisfactory results. A smaller area (or thicker) device would result in lower noise because of lower capacitance, and if the distance to the substrate is reduced, the signal remains constant. Detection of scattered light may have even a higher sensitivity.

An assumed area of 3×3 mm scanned in steps of 30 micron, at 1 msec per step will take 10 seconds to scan. If the detection array 100 has 1,000 sensors 102, then a total area of approximately 10×10 cm is scanned in 10 seconds and the resulting image contains $10^7$ pixels. The total illumination intensity used is 10 mW. Faster scanning may be accomplished by increasing the illumination intensity, reducing the spatial resolution, or reducing the sensor electronic noise by making it thicker.

This systems and methods of the invention may provide an inexpensive system with a high sensitivity and speed by having many sensors 102 operating in parallel, and high optical efficiency through the use of proximity detection.

While the invention has been described in conjunction with exemplary embodiment, these embodiments should be viewed as illustrative, not limiting. Various modifications, substitutes, or the like are possible within the spirit and scope of the invention.

What is claimed is:

1. A light detection system for imaging an object comprising:
    a light source;
    an object;
    a first substrate that includes a sensor arranged on a side of the first substrate opposite from the light source, the sensor having an opening through which the light from the light source passes, and a distance from the sensor to the object corresponds approximately to the size of the sensor,
    the light from the light source illuminating the object and the sensor detecting the light emanating from the object, and
    the sensor is in close proximity to the object, and the object is scanned relative to the sensor to create the image.

2. The light detection system of claim 1, wherein the light emanating from the object is one of at least fluorescence and reflected light.

3. The light detection system of claim 2, further comprising the light source being a laser that illuminates the object.

4. The light detection system of claim 1, further comprising the sensor being a photodiode configured to have a high rejection of direct excitation illumination.

5. The light detection system of claim 4, further comprising first and second electrodes formed on outer surfaces of the photodiode, the first electrode formed on the first substrate.

6. The light detection system of claim 1, further comprising an insulation layer formed on an inner surface of the sensor and surrounding the opening of the sensor.

7. The light detection system of claim 1, further comprising a filter arranged on a second substrate and facing the second electrode, the filter absorbing reflected excitation light from the light source, but not absorbing fluorescent light.

8. The light detection system of claim 5, further comprising the first electrode being formed of an opaque material to prevent scattered light from being detected by the sensor, and the second electrode being formed of a transparent material to allow fluorescent light to be detected by the sensor.

9. The light detection system of claim 1, further comprising a plurality of baffles being formed on each side of the sensor, the baffles being formed of one of at least a light reflective material and a light absorption material.

10. The light detection system of claim 1, further comprising a lens arranged on an opposite side of the first substrate from the sensor, the lens focusing the light from the light source on the object.

11. The light detection system of claim 1, further comprising the sensor detecting the light emanating from the object without the emanating light passing through a lens.

12. A method of detecting light for imaging an object, comprising:
    arranging a sensor with an opening to face the object and so that the distance from the sensor to the object corresponds approximately to the size of the sensor;
    illuminating the object with a light source so that the light passes through the opening in the sensor; and
    detecting the light emanating from the object,
    the object being scanned relative to the sensor to create the image.

13. The method of detecting light of claim 12, further comprising the light emanating from the object is one of at least fluorescent light and reflected light.

14. The method of detecting light of claim 13, further comprising illuminating the light source using a laser that illuminates the object.

15. The method of detecting light of claim 12, further comprising using a photodiode as the sensor that is configured to have a high rejection of direct excitation illumination.

16. The method of detecting light of claim 15, further comprising arranging the sensor on a first substrate and forming first and second electrodes on outer surfaces of the photodiode, the first electrode formed on the first substrate.

17. The method of detecting light of claim 12, further comprising forming an insulation layer on an inner surface of the sensor and surrounding the opening of the sensor.

18. The method of detecting light of claim 12, further comprising arranging a filter on a second substrate and facing the second electrode, the filter absorbing reflected excitation light from the light source, but not absorbing fluorescent light.

19. The method of detecting light of claim 16, further comprising forming the first electrode of an opaque material to prevent scattered light from being detected by the sensor, and forming the second electrode of a transparent material to allow fluorescent light to be detected by the sensor.

20. The method of detecting light of claim 12, further comprising forming a plurality of baffles on each side of the sensor, the baffles being formed of one of at least a light reflective material and a light absorption material.

21. The method of detecting light of claim 16, further comprising forming a lens on an opposite side of the first substrate from the sensor, the lens focusing the light from the light source on the object.

* * * * *